United States Patent
Zhang et al.

(10) Patent No.: US 11,545,239 B1
(45) Date of Patent: Jan. 3, 2023

(54) METHOD FOR PREDICTING YIELD OF CALCIUM IN A CALCIUM TREATMENT PROCESS BASED ON DEEP NEURAL NETWORK

(71) Applicants: North China University of Technology, Beijing (CN); Yanshan University, Qinhuangdao (CN); University of Science and Technology Beijing, Beijing (CN)

(72) Inventors: Lifeng Zhang, Beijing (CN); Weijian Wang, Beijing (CN); Qiang Ren, Qinhuangdao (CN); Ying Ren, Beijing (CN); Yan Luo, Beijing (CN)

(73) Assignees: NORTH CHINA UNIVERSITY OF TECHNOLOGY, Beijing (CN); YANSHAN UNIVERSITY, Qinhuangdao (CN); UNIVERSITY OF SCIENCE AND TECHNOLOGY BEIJING, Beijing (CN)

( * ) Notice: Subject to any disclaimer, the term of this patent is extended or adjusted under 35 U.S.C. 154(b) by 0 days.

(21) Appl. No.: 17/844,364

(22) Filed: Jun. 20, 2022

(30) Foreign Application Priority Data

Jun. 22, 2021 (CN) .......................... 202110691320.6

(51) Int. Cl.
*G16C 20/10* (2019.01)
*G16C 20/70* (2019.01)

(52) U.S. Cl.
CPC ............ *G16C 20/10* (2019.02); *G16C 20/70* (2019.02)

(58) Field of Classification Search
CPC .............................. G16C 20/10; G16C 20/70
See application file for complete search history.

(56) References Cited

U.S. PATENT DOCUMENTS

| 5,327,357 A | * | 7/1994 | Feinstein | ................ C21C 5/30 |
| | | | | 75/375 |
| 2012/0145353 A1 | * | 6/2012 | Nakayama | .............. C22B 9/006 |
| | | | | 164/493 |

(Continued)

FOREIGN PATENT DOCUMENTS

| CN | 110777230 A | * | 2/2020 | ............. B22D 11/11 |
| KR | 20030047589 A | * | 8/2008 | ................ C21C 7/06 |

OTHER PUBLICATIONS

Zhao, Liping., "Intelligent Prediction Method of Quality for Continuous Casting Process"., IEEE Xplore., 978-1-4673-9613-4/16/ $31.00 ©2016 IEEE (Year: 2016).*

Primary Examiner — Yoshihisa Ishizuka
(74) Attorney, Agent, or Firm — WPAT, PC

(57) ABSTRACT

A method for predicting a yield of calcium in a calcium treatment process based on deep neural network as provided relates to a calcium treatment process of molten steel refining in the field of iron and steel metallurgy, and includes steps of: obtaining production and operation data information of each of charges and thereby constructing a dataset; training and testing a deep neural network based on constructed dataset to establish a prediction model; and based on the prediction model, predicting and calculating current yield of calcium by taking actual production and operation data information of each charge as input. The method can predict the yield of calcium in the calcium treatment process, is favorable for accurately controlling a calcium content of steel, can stably control the calcium treatment process, improve the calcium treatment effect, improve the product quality, and ensure the production stability.

7 Claims, 1 Drawing Sheet

(56) References Cited

U.S. PATENT DOCUMENTS

2020/0257933 A1\* 8/2020 Steingrimsson ....... G16C 20/70
2022/0072593 A1\* 3/2022 Fujita .................... B22D 11/16

\* cited by examiner

METHOD FOR PREDICTING YIELD OF CALCIUM IN A CALCIUM TREATMENT PROCESS BASED ON DEEP NEURAL NETWORK

TECHNICAL FIELD

The invention relates to the field of molten steel refining in iron and steel metallurgy, in particularly to a method for predicting a yield of calcium in a calcium treatment process based on deep neural network.

BACKGROUND

In a smelting process of molten steel, in order to effectively reduce an oxygen content in molten steel to a low level, aluminum as a strong deoxidizer is widely used in a steelmaking process. However, an addition of aluminum would produce a large number of alumina inclusions, which would easily lead to nozzle clogging, affect a smooth running of continuous casting process and lead to the degradation of product performance. Therefore, calcium is added into the molten steel to modify the alumina inclusions in the molten steel into liquid calcium aluminate, thereby reduce the nozzle clogging, ensure smooth running of continuous casting and improve the product quality. Moreover, the presence of calcium in steel can also control the morphology and quantity of MnS inclusions in steel. However, there is a reasonable range of calcium requirement in steel. If an addition amount of calcium is low, which cannot achieve the effect of calcium treatment; whereas if the addition amount of calcium is too high, it is easy to produce high melting point CaS inclusions, which also easily lead to nozzle clogging.

In recent years, benefiting from the rapid development of computer and big data technology, neural networks have been widely used in various industries. The neural networks are self-learning and self-adaptive. When the environment changes, that is, when a new training sample is given to the neural network, the neural network can automatically adjust weights of interconnections, so as to give a reasonable expected output under certain input conditions. Moreover, the neural network has good fault tolerance, and local errors do not make the neural network produce more serious errors. The neural network has the ability to solve practical problems by constantly adjusting weights among respective neuron nodes.

Compared with alloys of aluminum, silicon and manganese, calcium has lower melting point and boiling point, a lower solubility in steel and a higher vapor pressure. Therefore, a calcium alloy is difficult to be added into the molten steel, and the calcium treatment process is difficult to control a calcium content in the molten steel within a certain range. For most iron and steel enterprises, the calcium treatment process is fed with calcium based on experience, and thus a yield of the calcium treatment process cannot be predicted, so that the control of calcium content is unstable. Therefore, how to predict a yield of calcium in the calcium treatment process based on deep neural network calculation is of great research value and significance for accurately controlling the calcium content in steel, stabilizing the calcium treatment operation, reducing production and operation costs of enterprises, and improving the product quality and alloy utilization efficiency.

SUMMARY

In order to solve the shortcomings of the related art, the invention provides a method for predicting a yield of calcium in a calcium treatment process based on deep neural network, for realizing the stable control of the calcium treatment operation consequently.

Specifically, an embodiment of the invention provides a method for predicting a yield of calcium in a calcium treatment process based on deep neural network, including:

S1, obtaining parameters affecting the yield of calcium in the calcium treatment process from production and operation data information, and thereby constructing a dataset; wherein the S1 specifically includes:

S11, collecting production and operation data information in a refining process of each production charge and calculating the yield of calcium of each the production charge, as a piece of record; wherein the yield of calcium of each the production charge includes a yield of calcium $\eta_1$ in the refining process, a yield of calcium $\eta_2$ of tundish, and a yield of calcium $\eta_3$ of continuous casting billet;

a calculation formula for the yield of calcium in the refining process is that:

$$\eta_1 = \frac{W(\omega[Ca]_R - \omega[Ca]_o)}{\chi\beta\mu} \times 10^3,$$

a calculation formula for the yield of calcium of tundish is that:

$$\eta_2 = \frac{W(\omega[Ca]_T - \omega[Ca]_o)}{\chi\beta\mu} \times 10^3,$$

a calculation formula for the yield of calcium of continuous casting billet is that:

$$\eta_3 = \frac{W(\omega[Ca]_B - \omega[Ca]_o)}{\chi\beta\mu} \times 10^3,$$

where, W represents a molten steel weight, with a unit of ton (t); $\omega[Ca]_o$ represents a calcium content of molten steel before calcium treatment, with a unit of parts per million (ppm); $\chi$ represents a calcium wire feeding length, with a unit of meter (m); $\beta$ represents a calcium content of calcium wire, with a unit of %; $\mu$ represents a meter weight of calcium wire, with a unit of kilogram per meter (kg/m); $\omega[Ca]_R$ represents a calcium content of molten steel after the refining process, with a unit of ppm; $\omega[Ca]_T$ represents a calcium content of molten steel in a tundish during continuous casting, with a unit of ppm; and $\omega[Ca]_B$ represents a calcium content in a continuous casting billet, with a unit of ppm;

S12, repeatedly collecting the production and operation data information in the refining process of each production charge, and thereby establishing a dataset; and S13, preprocessing the dataset established in the S12 to remove incomplete data and unreasonable data;

S2, performing normalization processing on the dataset constructed in the S1 to obtain a normalized dataset;

S3, building a deep neural network, comprising: dividing the normalized dataset obtained in the S2 into a training dataset and a testing dataset, using production and operation data information as input of the deep neural network and using an actual yield of calcium as output of the deep neural network, comparing a calculation result with an actual result, modifying weights and thresholds, and using data in the training dataset to train the deep neural network, thereby obtaining a trained deep neural network;

S4, using the testing dataset to test the trained deep neural network obtained in the S3, using input data in the testing dataset as input data of the trained deep neural network to obtain calculation results of yield of calcium, and taking an error generated by actual results of yield of calcium and the calculation results of yield of calcium of the trained deep neural network reaches a minimum threshold as an optimization objective to optimize the trained deep neural network;

S5, determining, based on the error in the S4, the trained deep neural network whether meets a requirement or not; in response to the error reaches the minimum threshold, taking current trained deep neural network as a resultant prediction model of yield of calcium; in response to the error does not reach the minimum threshold, modifying a hidden layer quantity, a node quantity, and a learning rate of the trained deep neural network, and repeating the S4 until the error reaches the minimum threshold which indicates a yield of calcium calculated by the trained deep neural network meets a predetermined requirement; and S6, predicting a yield of calcium in an actual calcium treatment process based on the resultant prediction model of yield of calcium obtained in the S5.

In a preferred embodiment, the parameters affecting the yield of calcium in the calcium treatment process in the S1 include: a carbon (C) content of molten steel, a silicon (Si) content of molten steel, a manganese (Mn) content of molten, a phosphorus (P) content of molten steel, a sulfur (S) content of molten steel, a free-oxygen content of molten steel, a molten steel temperature, a calcium wire type, a calcium wire feeding speed, an argon blowing flow rate, a molten steel weight, a calcium wire feeding length, type and quantity of raw and auxiliary materials added in the refining process, and a calcium content of calcium wire.

In a preferred embodiment, during the collecting in the S11, performing samplings before and after calcium treatment to test a composition of molten steel, while placing a sampler into a same position of a steel ladle during the samplings;

during detecting a composition of molten steel in the tundish, performing samplings at a same position of the tundish at half of pouring; and during detecting a composition of continuous casting billet, taking a continuous casting billet of stabilized pouring, and sampling at a position of ¼ of a plate width and ¼ distance from an inner arc side for analysis.

In a preferred embodiment, the composition of molten steel before calcium treatment is detected through spark direct reading spectrometer method, including: firstly polishing a sample, then exciting at least two points on a surface of polished sample, observing a composition of each of excited points and deleting the point with larger composition deviation, until a stable detection result is obtained; and an oxygen probe is used to measure the molten steel temperature and a content of dissolved oxygen when molten steel enters a station after calcium treatment, and the oxygen probe is inserted into the same position of molten steel.

In a preferred embodiment, training of the deep neural network in the S3 includes following sub-steps:

S31, initializing weights and thresholds of each layer by using a small random number; calculating, backwards from a first layer of network, outputs of neurons according to set network structure and weights and thresholds of a preceding iteration; then modifying the weights and the thresholds, calculating, forwards from a last layer, an influence of the thresholds and the weights to a total error, and adjusting the weights and the thresholds based on an error; wherein the two processes are alternately performed until convergence is reached; and S32, a transfer function between the neurons using Sigmoid function and employing the following formulas:

$$y_i = f\left(\sum_{j=1}^{n} w_{ij} x_j - \theta_i\right)$$

$$f(X) = \frac{1}{1+e^{-X}}$$

where, X represents a normalized X variable, w represents a weight of connection between the neurons, and θ represents a threshold of neuron node.

In a preferred embodiment, the deep neural network built in the S3 has an input layer containing 21 nodes, has 3 middle layers each of which contains 6 nodes, has an output layer containing one node, has a maximum number of iterations of 1500, and has a learning rate of 0.2. In some embodiments, the deep neural network built in the S3 has an input layer containing 15-25 nodes, has 1-6 middle layers each of which contains 1-10 nodes, has an output layer containing one node, has a maximum number of iterations of 1500, and has a learning rate of 0.1-0.5.

In a preferred embodiment, the minimum threshold of the error is 5%.

Compared with the related art, the invention may achieve the following beneficial effects:

In the method for predicting the yield of calcium in the calcium treatment process based on deep neural network, a dataset is constructed by obtaining operation parameter information of each production charge in advance, a deep neural network model is built based on constructed dataset as a prediction model, production operation information of each charge are obtained, and prediction is carried out based on deep neural network to obtain a reasonable yield of calcium in current charge as a reference basis for calcium treatment operation. By using this model to predict and calculate the yield of calcium, the yield of calcium can be stably controlled and improved. For some steel grades, by adjusting operation parameters of calcium feeding, the yield of calcium can be increased from 10%-20% to 30% or more, which can reduce the feeding amount of calcium and thereby reduce the production cost. The reasonable feeding amount of calcium can also reduce the occurrence of nozzle clogging, thereby ensuring the smooth running of continuous casting process, and improving the production efficiency and the product quality.

DETAILED DESCRIPTION OF EMBODIMENTS

Figure 1:
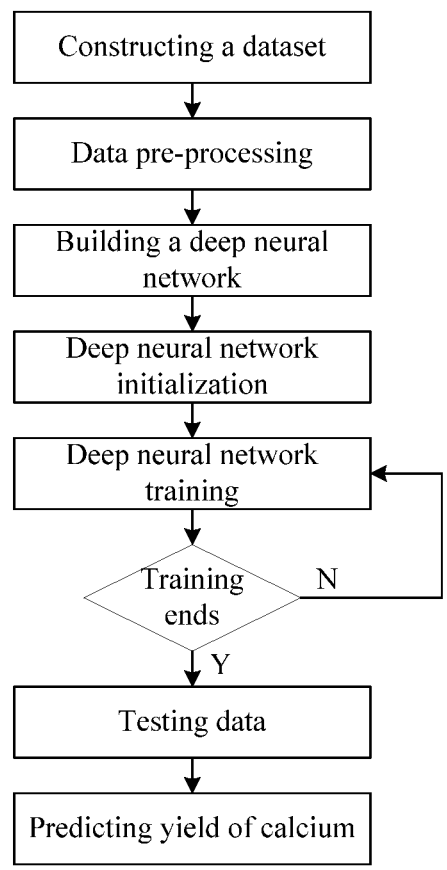
FIG. 1 illustrates a flowchart of a method for predicting a yield of calcium in a calcium treatment process of molten steel based on deep neural according to an embodiment of the invention.

Illustrative embodiments, features, and aspects of the invention will be described in detail below with reference to the accompanying drawings. Like reference numerals in the drawings indicate functionally identical or similar elements. Although various aspects of the embodiments are shown in the drawings, the drawings are not necessarily drawn to scale unless otherwise indicated.

According to an embodiment of the invention, a method for predicting a yield of calcium in a calcium treatment process of molten steel based on deep neural network is provided.

As shown in FIG. 1, the method for predicting a yield of calcium in a calcium treatment process of molten steel according to the illustrated embodiment may include step 1 through step 5 as follows.

Step 1, obtaining production and operation data information of a steel grade employing a calcium treatment process of a domestic factory in recent one year in advance, including a carbon (C) content of molten steel, a silicon (Si) content of molten steel, a manganese (Mn) content of molten, a phosphorus (P) content of molten steel, a sulfur (S) content of molten steel, a free-oxygen content of molten steel, a molten steel temperature, a calcium wire type, a calcium wire feeding speed, an argon blowing flow rate, a molten steel weight, a calcium wire feeding length, type and quantity of raw and auxiliary materials added in a refining process, and a calcium content of calcium wire, totaling 561 groups of data; calculating yields of calcium in the calcium treatment process and constructing a dataset.

The step 1 may specifically include the sub-step S11 as follows:

S11, collecting production and operation data information in a refining process of each production charge and calculating a yield of calcium of each production charge, as a piece of record.

A calculation formula of the yield of calcium in the refining process is that:

$$\eta_1 = \frac{W(\omega[Ca]_R - \omega[Ca]_o)}{\chi\beta\mu} \times 10^3.$$

A calculation formula of a yield of calcium of a tundish is that:

$$\eta_2 = \frac{W(\omega[Ca]_T - \omega[Ca]_o)}{\chi\beta\mu} \times 10^3.$$

A calculation formula of a yield of calcium of a continuous casting billet is that:

$$\eta_3 = \frac{W(\omega[Ca]_B - \omega[Ca]_o)}{\chi\beta\mu} \times 10^3.$$

Where, W represents the molten steel weight, with a unit of t (ton); $\omega[Ca]_o$ represents the calcium content of molten steel before calcium treatment, with a unit of ppm (abbreviation for parts per million); $\chi$ represents the calcium wire feeding length, with a unit of m (meter); $\beta$ represents the calcium content of calcium wire, with a unit of % (percentage); $\mu$ represents a meter weight of calcium wire, with a unit of kg/m (kilogram per meter); $\omega[Ca]_R$ represents the calcium content of molten steel after refining, with a unit of ppm; $\omega[Ca]_T$ represents the calcium content of molten steel in a tundish during continuous casting, with a unit of ppm; and, $\omega[Ca]_B$ represents the calcium content in a continuous casting billet, with a unit of ppm.

Step 2, performing normalization processing on the dataset obtained in the step 1 to obtain a normalized dataset.

For the normalization processing of the dataset in the step 2, a normalization method uses the following formula:

$$y = (y_{max} - y_{min}) \times \frac{x - x_{min}}{x_{max} - x_{min}} + y_{min},$$

where, $y_{min}$ and $y_{max}$ respectively represent normalized minimum value and maximum value, and respectively may be −1 and 1 in the illustrated embodiment; $X_{min}$ and $X_{max}$ respectively represent a minimum value and a maximum value of a variable X.

Step 3, dividing the dataset obtained by the step 2 into a training dataset and a testing dataset, randomly selecting S11 groups of data as the training dataset and 50 groups of data as the testing dataset, building a deep neural network by using data such as composition data of molten steel and operation conditions of calcium feeding as input and actual yields of calcium as output, and training built deep neural network by the data in the training dataset.

Step 4, testing trained deep neural network obtained in the step 3 by the testing dataset. In particular, input data in the testing dataset are used as input data of the deep neural network to obtain calculation results of yield of calcium, an error generated by actual results of yield of calcium and the calculation results of yield of calcium of the trained deep neural network reaching a minimum threshold is taken as an optimization objective, and the minimum threshold of the optimization objective of the error is preferably set as 5%.

A calculation formula for the error generated by the actual results of yield of calcium and the calculation results of yield of calcium of the trained deep neural network is that:

$$RMSE = \sqrt{\frac{\sum(Y_{Cal} - Y_{Exp})^2}{n}}$$

where, $Y_{Cal}$ represents the yield of calcium calculated by the deep neural network, $Y_{Exp}$ represents the actual yield of calcium, and n represents a quantity of selected testing data.

Figure 2:
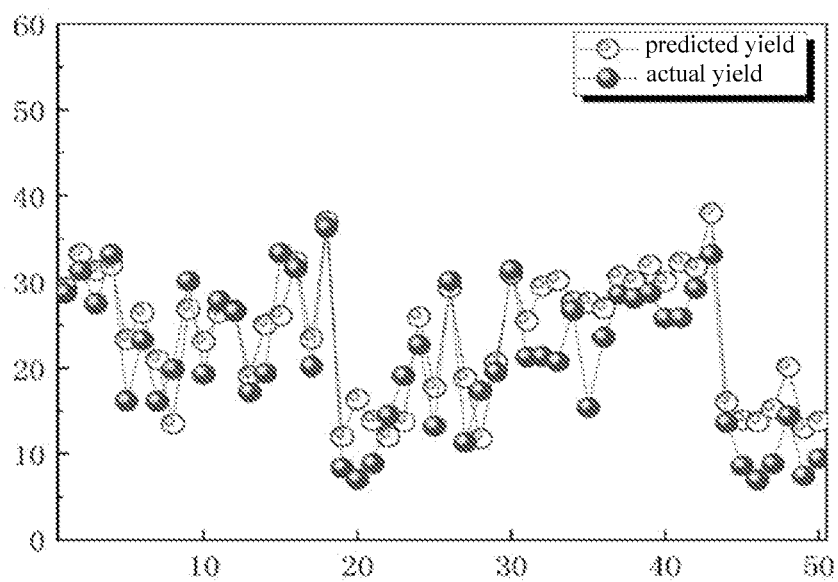
FIG. 2 illustrates a schematic diagram of showing comparison of yields calculated based on a deep neural network model with actual results.

Step 5, determining the trained deep neural network whether meets a requirement or not based on the error calculated in the step 4; if yes, using current trained deep neural network as a prediction model of the yield of calcium; whereas if not, modifying structural parameters of the trained deep neural network, and repeating the step 4 until the yield of calcium calculated by the trained depth neural network meets a predetermined requirement. FIG. 2 illustrated a comparison result of yields of calcium predicted by the trained deep neural network with actual yields of calcium, and an error between current prediction result of yield of calcium and the actual yield of calcium is less than 5%.

In an embodiment, the structural parameters of the deep neural network include a hidden layer quantity, a node quantity in each hidden layer, and a learning rate.

Step 6, predicting a yield of calcium in an actual calcium treatment process according to the trained deep neural network model obtained by the step 5.

The obtaining of the data in advance and the constructing of the dataset in the step 1 may include the following step:

collecting information of various parameters in the refining process of each production charge, as a piece of record;

wherein the information of various parameters of each the production charge may include: contents of C, Si, Mn, P, S, Al, O, and Ca of molten steel before calcium treatment, a molten steel temperature, a molten steel weight, weights of a modifier, a desulfurizer, a carburant, and lime added during refining, a calcium wire feeding speed, and an argon blowing flow rate, etc.

Samplings may be carried out before and after calcium treatment to test the composition of molten steel. In order to ensure the stability of sampling results, a sampler shall be placed at a same position of a steel ladle during the samplings, to ensure the samplings at the same position.

The composition of molten steel before the calcium treatment may be detected by spark direct-reading spectrometer method, which may include: firstly, polishing a sample to be bright, and then exciting at least two points on a surface of the sample and observing compositions of the excited points and deleting the point with larger composition deviation, until a stable detection result is obtained. When the molten steel enters a station, an oxygen probe is used to measure the molten steel temperature and the content of dissolved oxygen, and the oxygen probe is ensured to be inserted into the same position of the molten steel.

Specific steps of training the deep neural network in the step 3 may be as follows:

initializing weights and thresholds of each layer by using a small random number, calculating, backwards from the first layer of the network, outputs of respective neurons through set network structure and weights and thresholds of the preceding iteration, then modifying the weights and the thresholds, and calculating, forwards from the last layer, an influence of the thresholds and the weights to a total error, and adjusting the weights and the threshold according to an error. The two processes are alternately carried out until convergence is reached; and a transfer function between neurons using the Sigmoid function and employing the formulas as follows:

$$y_i = f\left(\sum_{j=1}^{n} w_{ij} x_j - \theta_i\right)$$

$$f(X) = \frac{1}{1+e^{-X}}$$

where, X represents the normalized variable X, w represents a weight of connection between neurons, and $\theta$ represents a threshold of neuron node.

For the built deep neural network, the input layer contains 21 nodes, there is three middle layers and each the middle layer contains 6 nodes, and the output layer contains one node. The maximum number of iterations may be 1500, and the learning rate may be 0.2.

The deep neural network model is trained based on the constructed dataset until the error of the deep neural network model stabilizes at a small value, indicating that the deep neural network has converged. By using the trained deep neural network, a yield of calcium under current production conditions can be predicted after obtaining relevant operation parameter information of each charge before calcium treatment.

According to the invention, a yield of calcium in a calcium treatment process of molten steel can be predicted by collecting operation parameter information before calcium treatment of molten steel, which can more stably control a calcium content in the calcium treatment process, and thereby improve the calcium treatment effect, reduce the production cost, and improve the production efficiency and product quality.

Finally, it should be noted that the above embodiments are only used to illustrate the technical solutions of the invention, rather than limiting the invention. Although the invention has been described in detail with reference to the foregoing embodiments, those skilled in the art should understand that the technical solutions described in the foregoing embodiments can still be modified, or some or all of the technical features thereof can be equivalently substituted; and these modifications or substitutions do not cause essences of the corresponding technical solutions to deviate from scopes of the technical solutions of the embodiments of the invention.

What is claimed is:

1. A method for predicting a yield of calcium in a calcium treatment process based on deep neural network, comprising:

S1, obtaining parameters affecting the yield of calcium in the calcium treatment process from production and operation data information, and thereby constructing a dataset; wherein the S1 comprises:

S11, collecting production and operation data information in a refining process of each production charge and calculating the yield of calcium of each the production charge, as a piece of record;

wherein the yield of calcium of each the production charge comprises a yield of calcium $\eta_1$ in the refining process, a yield of calcium $\eta_2$ of tundish, and a yield of calcium $\eta_3$ of continuous casting billet;

a calculation formula for the yield of calcium in the refining process is that:

$$\eta_1 = \frac{W(\omega[\text{Ca}]_R - \omega[\text{Ca}]_o)}{\chi \beta \mu} \times 10^3,$$

a calculation formula for the yield of calcium of tundish is that:

$$\eta_2 = \frac{W(\omega[\text{Ca}]_T - \omega[\text{Ca}]_o)}{\chi \beta \mu} \times 10^3,$$

a calculation formula for the yield of calcium of continuous casting billet is that:

$$\eta_3 = \frac{W(\omega[\text{Ca}]_B - \omega[\text{Ca}]_o)}{\chi \beta \mu} \times 10^3,$$

where, W represents a molten steel weight, with a unit of ton (t); $\omega[\text{Ca}]_o$ represents a calcium content of molten steel before calcium treatment, with a unit of parts per million (ppm); $\chi$ represents a calcium wire feeding length, with a unit of meter (m); $\beta$ represents a calcium content of calcium wire, with a unit of %; $\mu$ represents a meter weight of calcium wire, with a unit of kilogram per meter (kg/m); $\omega[\text{Ca}]_R$ represents a calcium content of molten steel after the refining process, with a unit of ppm; ω[Ca]$_T$ represents a calcium content of molten steel in a tundish during continuous casting, with a unit of ppm; and ω[Ca]$_B$ represents a calcium content in a continuous casting billet, with a unit of ppm;

S12, repeatedly collecting the production and operation data information in the refining process of each production charge, and thereby establishing a dataset; and S13, preprocessing the dataset established in the S12 to remove incomplete data and unreasonable data;

S2, performing normalization processing on the dataset constructed in the S1 to obtain a normalized dataset;

S3, building a deep neural network, comprising: dividing the normalized dataset obtained in the S2 into a training dataset and a testing dataset, using production and operation data information as input of the deep neural network and using an actual yield of calcium as output of the deep neural network, comparing a calculation result with an actual result, modifying weights and thresholds, and using data in the training dataset to train the deep neural network, thereby obtaining a trained deep neural network;

S4, using the testing dataset to test the trained deep neural network obtained in the S3, using input data in the testing dataset as input data of the trained deep neural network to obtain calculation results of yield of calcium, and taking an error generated by actual results of yield of calcium and the calculation results of yield of calcium of the trained deep neural network reaches a minimum threshold as an optimization objective to optimize the trained deep neural network;

S5, determining, based on the error in the S4, the trained deep neural network whether meets a requirement or not; in response to the error reaches the minimum threshold, taking current trained deep neural network as a resultant prediction model of yield of calcium; in response to the error does not reach the minimum threshold, modifying a hidden layer quantity, a node quantity, and a learning rate of the trained deep neural network, and repeating the S4 until the error reaches the minimum threshold which indicates a yield of calcium calculated by the trained deep neural network meets a predetermined requirement; and S6, predicting a yield of calcium in an actual calcium treatment process based on the resultant prediction model of yield of calcium obtained in the S5.

2. The method for predicting a yield of calcium in a calcium treatment process based on deep neural network as claimed in claim 1, wherein the parameters affecting the yield of calcium in the calcium treatment process in the S11 comprise: a carbon (C) content of molten steel, a silicon (Si) content of molten steel, a manganese (Mn) content of molten, a phosphorus (P) content of molten steel, a sulfur (S) content of molten steel, a free-oxygen content of molten steel, a molten steel temperature, a calcium wire type, a calcium wire feeding speed, an argon blowing flow rate, a molten steel weight, a calcium wire feeding length, type and quantity of raw and auxiliary materials added in the refining process, and a calcium content of calcium wire.

3. The method for predicting a yield of calcium in a calcium treatment process based on deep neural network as claimed in claim 2, wherein during the collecting in the S11, performing samplings before and after calcium treatment to test a composition of molten steel, while placing a sampler into a same position of a steel ladle during the samplings; during detecting a composition of molten steel in the tundish, performing samplings at a same position of the tundish at half of pouring;

during detecting a composition of continuous casting billet, taking a continuous casting billet of stabilized pouring, and sampling at a position of ¼ of a plate width and ¼ distance from an inner arc side for analysis.

4. The method for predicting a yield of calcium in a calcium treatment process based on deep neural network as claimed in claim 3, wherein the composition of molten steel before calcium treatment is detected through spark direct reading spectrometer method, including: firstly polishing a sample, then exciting at least two points on a surface of polished sample, observing a composition of each of excited points and deleting the point with larger composition deviation, until a stable detection result is obtained; and an oxygen probe is used to measure the molten steel temperature and a content of dissolved oxygen when molten steel enters a station after calcium treatment, and the oxygen probe is inserted into the same position of molten steel.

5. The method for predicting a yield of calcium in a calcium treatment process based on deep neural network as claimed in claim 1, wherein training of the deep neural network in the S3 comprises following sub-steps:

S31, initializing weights and thresholds of each layer by using a small random number; calculating, backwards from a first layer of network, outputs of neurons according to set network structure and weights and thresholds of a preceding iteration; then modifying the weights and the thresholds, calculating, forwards from a last layer, an influence of the thresholds and the weights to a total error, and adjusting the weights and the thresholds based on an error; wherein the two processes are alternately performed until convergence is reached; and S2, a transfer function between the neurons using Sigmoid function and employing the following formulas:

$$y_i = f\left(\sum_{j=1}^{n} w_{ij}x_j - \theta_i\right)$$

$$f(X) = \frac{1}{1 + e^{-X}}$$

where, X represents a normalized X variable, w represents a weight of connection between the neurons, and θ represents a threshold of neuron node.

6. The method for predicting a yield of calcium in a calcium treatment process based on deep neural network as claimed in claim 5, wherein the deep neural network built in the S3 has an input layer containing 15-25 nodes, has 1-6 middle layers each of which contains 1-10 nodes, has an output layer containing one node, has a maximum number of iterations of 1500, and has a learning rate of 0.1-0.5.

7. The method for predicting a yield of calcium in a calcium treatment process based on deep neural network as claimed in claim 1, wherein the minimum threshold of the error is 5%.

* * * * *